(12) United States Patent
Grassauer et al.

(10) Patent No.: US 10,660,914 B2
(45) Date of Patent: May 26, 2020

(54) STUFFY NOSE DEBLOCKING COMPOSITION HAVING ANTIVIRAL ACTIVITY

(71) Applicant: MARINOMED BIOTECH AG, Vienna (AT)

(72) Inventors: Andreas Grassauer, Vienna (AT); Eva Prieschl-Grassauer, Vienna (AT); Angelika Bodenteich, Vienna (AT); Christiane Koller, Seyring/Gerasdorf (AT); Martina Morokutti-Kurz, Vienna (AT)

(73) Assignee: MARINOMED BIOTECH AG, Vienna (AT)

( * ) Notice: Subject to any disclaimer, the term of this patent is extended or adjusted under 35 U.S.C. 154(b) by 0 days.

(21) Appl. No.: 15/767,273

(22) PCT Filed: Jul. 12, 2016

(86) PCT No.: PCT/EP2016/066565
§ 371 (c)(1),
(2) Date: Apr. 10, 2018

(87) PCT Pub. No.: WO2017/009351
PCT Pub. Date: Jan. 19, 2017

(65) Prior Publication Data
US 2019/0060358 A1 Feb. 28, 2019

(30) Foreign Application Priority Data

Jul. 14, 2015 (EP) .................................... 15176670

(51) Int. Cl.
| | | |
|---|---|---|
| *A61K 33/14* | (2006.01) | |
| *A61K 9/00* | (2006.01) | |
| *A61K 31/731* | (2006.01) | |
| *A61K 9/08* | (2006.01) | |
| *A61K 31/047* | (2006.01) | |
| *A61K 45/06* | (2006.01) | |
| *A61K 47/26* | (2006.01) | |
| *A61K 9/12* | (2006.01) | |
| *A61P 31/14* | (2006.01) | |
| *A61P 11/02* | (2006.01) | |

(52) U.S. Cl.
CPC ............ *A61K 33/14* (2013.01); *A61K 9/0043* (2013.01); *A61K 9/08* (2013.01); *A61K 9/12* (2013.01); *A61K 31/047* (2013.01); *A61K 31/731* (2013.01); *A61K 45/06* (2013.01); *A61K 47/26* (2013.01); *A61P 11/02* (2018.01); *A61P 31/14* (2018.01)

(58) Field of Classification Search
CPC ...... A61K 31/731; A61K 9/0043; A61P 11/02
See application file for complete search history.

(56) References Cited

U.S. PATENT DOCUMENTS

| 8,557,871 B2 | 10/2013 | Louis et al. | |
|---|---|---|---|
| 2006/0110331 A1* | 5/2006 | Dang | A61K 9/0043 424/45 |
| 2008/0241271 A1* | 10/2008 | Roman | A61K 9/0043 424/641 |
| 2011/0059919 A1* | 3/2011 | Grassauer | A61K 31/737 514/54 |
| 2011/0077296 A1* | 3/2011 | Hensley | A61K 9/0043 514/494 |

FOREIGN PATENT DOCUMENTS

| EP | 0424043 A1 | 4/1991 |
|---|---|---|
| WO | 2008/067982 A2 | 6/2008 |
| WO | 2009/027057 A1 | 3/2009 |
| WO | 2013/049538 A1 | 4/2013 |

OTHER PUBLICATIONS

Eccles, R. et al. "Efficacy and safety of an antiviral Iota-Carrageenan nasal spray: a randomized, double-blind, placebo-controlled exploratory study in volunteers with early symptoms of the" Respiratory Research 2010, 11:108, pp. 1-10. (Year: 2010).*
Song et al., "The Influence of Stabilizer and Bioadhesive Polymer on the Permeation-Enhancing Effect of AT1002 in the Nasal Delivery of a Paracellular Marker," Archives of Pharmacal Research, vol. 35, No. 2, Feb. 28, 2012, pp. 359-366.
Ramakrishnan et al., Behavior of k-carrageenan in glycerol and sorbitol solutions, Carbohydrate Polymers, vol. 13, No. 4, Dec. 1, 2000, pp. 327-332.
Eccles et al., Efficacy and safety of an antiviral Iota-Carrageenan nasal spray: a randomized, double-blind, placebo-controlled exploratory study in volunteers with early symptoms of the common cold, Resipratory Research, vol. 11, No. 1, Aug. 10, 2010, pp. 1-10.
Damiani et al., "Long-term Efficacy of Narivent in the Treatment of Nasal Congestion," The Open Medical Devices Journal, vol. 4, No. 1, Sep. 20, 2012, pp. 73-79.
Sep. 12, 2016 International Search Report issued in International Application No. PCT/EP2016/066565.
Sep. 12, 2016 Written Opinion issued in International Application No. PCT/EP2016/066565.
Gelcarin GP-379 Carrageenan, NF Datasheet dated Jan. 1, 2003.

* cited by examiner

*Primary Examiner* — Andrew S Rosenthal
(74) *Attorney, Agent, or Firm* — Oliff PLC

(57) ABSTRACT

A pharmaceutical composition has a stuffy nose deblocking activity. The composition includes a hyperosmolar aqueous solution of a non-ionic osmolality adjusting agent, optionally in combination with an ionic osmolality adjusting agent, wherein the composition further includes iota-carrageenan and/or kappa-carrageenan as an active antiviral ingredient in an antivirally effective amount, with the proviso that the composition in its ready-for-use formulation contains no more than 0-1.5% w/v of the ionic osmolality adjusting agent. The composition is useful for deblocking a stuffy nose and for prophylactic or therapeutic intervention of a number of viral infections of the upper respiratory tract.

20 Claims, No Drawings

STUFFY NOSE DEBLOCKING COMPOSITION HAVING ANTIVIRAL ACTIVITY

TECHNICAL FIELD

The present invention is in the field of physiology and immunology and relates to the treatment of nasal congestion, respiratory viral infection, and allergy.

BACKGROUND OF THE INVENTION

Viral infections of the respiratory tract as well as allergic reactions triggered by pollen or other allergens result in an immunological response to the different triggers. In both indications a wide variety of entities can cause similar symptoms. Viral infections of the respiratory tract are caused by more than 150 different viruses from the families of human rhinoviruses (more than 100 serotypes), human corona viruses, members of the paramyxoviridae such as parainfluenza virus (1-4), metapneumovirus, respiratory syncytial viruses, members of the orthomyxoviridae such as influenza (A, B, C), bocavirus, and more. Allergic reactions in the nasal cavity may be seasonal due to allergy against particular pollen or similar temporary allergens, or perennial due to allergy against antigens derived from house dust mite, cats, dogs, other pets, and the like.

A key symptom in respiratory viral infection and allergy is a blocked and runny nose. Hyperosmolar nasal sprays are commonly used to reduce temporary nasal congestion independent of the cause of such a nasal congestion. Due to the higher osmotic pressure of the nasal spray relative to the cellular compartments, liquid is sucked from the cells to the exterior whereby the edema is reduced. A combination of a hyperosmolar solution and carrageenan would exert an anti-edemic activity due to the increased osmolality and an antiviral activity due to the known antiviral efficacy of carrageenan. Iota-carrageenan and a combination of iota- and kappa-carrageenan have been shown in the art to reduce the replication of respiratory viruses in vitro, in vivo and also in clinical trials in humans suffering from common cold, flu-like diseases and influenza, as reported, for example, in WO2008/067982 and WO2009/027057. Carrageenan nasal sprays require repetitive application for several days in order to be effective against viral infections of the upper respiratory tract. Whereas the application of a typical hyperosmolar solution has an immediate shrinking effect on the swollen mucosa of a blocked nose.

It would therefore be beneficial to have a pharmaceutical composition that would combine the benefits of an immediately acting stuffy nose deblocking agent and an antiviral and/or antiallergic effective compound.

The preparation disclosed herein successfully combines these benefits as will be set out in more detail hereinafter. In particular, the newly developed formulation acts as an antiviral treatment with all its associated benefits and, in addition, exerts an immediate effect on a blocked nose. In case of patients suffering from an allergic reaction in the nasal cavity the newly developed formulation provides additional relief due to its antiviral activity. It is known in the art that respiratory viral infections can lead to substantial worsening of an existing allergic disease. For example, it is accepted medical knowledge that patients suffering from hay fever have an increased risk of developing allergic asthma if they are hit by recurrent viral infections of the respiratory tract.

The use of carrageenans in nasal sprays is known in the art. Especially iota- and kappa-carrageenans are well tolerated and unlike lambda-carrageenan they do not promote any inflammatory processes. In addition, carrageenans are widely used as excipients and viscosifiers in the pharmaceutical, cosmetic, and food industries.

BRIEF DESCRIPTION OF THE INVENTION

The term "hyperosmolar" as used herein refers to any solution exerting an osmotic pressure higher than the one generated by a physiological, i.e. 0.9% wt, sodium chloride solution.

Hyperosmolar solutions of nasal sprays usually contain sodium chloride in concentrations of up to 3% by weight. It has been found that carrageenans are responsive to the presence of various cations, such as sodium, potassium, calcium or magnesium ions, in that they may change their polymeric secondary structure from a random structure to a more helical parallel structure. This change in structure effects both the viscosity of aqueous solutions containing the carrageenan polymer and the activity of the polymer against particular viruses, such as human rhinoviruses. It has further been recognized that higher cationic salt concentrations lead to more viscous solutions and to significant losses in antiviral activity of the carrageenans, particularly against human rhinoviruses, as evidenced by substantially increased $IC_{50}$ values of iota-carrageenan in the treatment of HRV1a and HRV8 infections. Similarly, the minimal inhibitory concentration required for the inhibition of human coronavirus OC43 has been found to be increased up to 10-fold in carrageenan preparations containing hyperosmolar concentrations of sodium chloride relative to isoosmolar preparations. It can therefore be concluded that an attempt to provide an antivirally active, nose deblocking preparation comprising a hyperosmolar sodium chloride solution together with carrageenan will most likely fail.

It has now surprisingly been found that carrageenan—and in particular iota-carrageenan or a combination of iota- and kappa-carrageenan—can be formulated into a novel pharmaceutical composition to combine the antiviral efficacy with a decongestant activity.

"Decongestant activity" as used herein shall relate to any activity of the novel preparations referred to herein that leads to a partial or full deblocking of a temporarily blocked, stuffy nose, irrespective of the cause of such temporary blocking of the nose such as, for example, an allergic or viral impairment.

The solution to the problem has been derived from the observation that a nonionic osmolality adjusting agent, hereinafter also called a non-ionic "osmolality giver", such as sorbitol, mannitol or glucose, may totally or partially replace the previously applied ionic osmolality giver, typically sodium chloride, in a carrageenan based nose-deblocking preparation. It has now been confirmed by experimental evidence that iota and/or kappa carrageenan will remain antivirally effective in a nose deblocking preparation at a level comparable to hypoosmolar carrageenan solutions comprising sodium chloride as the sole osmolality giver at concentrations of less than 0.9% w/v, e.g. at 0.5% w/v. This goal is achieved by providing the carrageenan component in a hyper-osmolar solution comprising either no cationic source such as an alkali or earth alkali metal salt, for example sodium chloride or, in the alternative, comprising a slightly hyperosmolar, an isoosmolar or a hypoosmolar concentration of such a salt together with a short-chain sugar selected from the group of mono-, di-, and oligosaccharides, and/or together with a sugar alcohol, i.e. polyol such as sorbitol, in an amount suitable to render the final solution sufficiently hyper-osmolar for the desired purpose, as set out hereinafter.

Summarizing the results clear proof was obtained that the antiviral properties of the preferred iota and kappa carrageenans can be retained in hyperosmolar nose-deblocking preparations by replacing a commonly used osmolarity enhancing salt such as sodium chloride with a non-ionic osmolarity or osmolality adjusting agent such as a short-chain sugar or polyol component. As opposed to the novel preparations, hyper-osmolar carrageenan preparations comprising NaCl as the only one osmolality adjusting agent, for example carrageenan preparations comprising 2.3% or 2.6% w/v NaCl as shown hereinafter, suffer from the big disadvantage that they are highly viscous and sterile filtration is almost impossible for such preparations.

Where the relative concentrations of ingredients of the present hyperosmolar compositions are given in percent [%], they shall be understood as referring to percent weight by volume (w/v), e.g. grams per liter, unless explicitly stated otherwise.

DETAILED DESCRIPTION OF THE INVENTION

Surprisingly, a hyperosmolar aqueous solution comprising a carrageenan component, typically iota- and/or kappa carrageenan, together with 0.5% NaCl and 7% to 10% sorbitol, is low in viscosity and sterile filtration of said solution is possible. The solution can also be pH-stabilized with a buffer and EDTA. It is therefore an object of the present invention to provide for a pharmaceutical preparation comprising carrageenan in a hyperosmolar solution, preferably iota-carrageenan and/or kappa-carrageenan, in an aqueous solution comprising a nonionic osmolality adjusting agent selected from the group of mono-, di-, tri-, and oligosaccharides, and polyols, and optionally further comprising an ionic osmolality giver such as, for example, sodium or potassium chloride, at a hypoosmolar, isoosmolar, or slightly hyperosmolar concentration. The hyperosmolar preparations referred to herein are useful as medicaments with decongestant, i.e. nose deblocking, mucosa shrinking activity and additionally convey antiviral activity useful in the prophylactic or therapeutic treatment of respiratory viral infections including those frequently caused by human rhinovirus, human coronavirus, members of the paramyxoviridae, members of the orthomyxoviridae, members of the adenoviridae, and other respiratory viruses.

In an embodiment of the invention, a pharmaceutical composition is provided that is primarily designed to reduce a temporary congestion of the nasal cavity.

"Nasal congestion" as referred to herein is of a temporary nature and may be the result of an infection in the nasal cavity by viruses or bacteria or may be due to an allergic reaction of an individual's body, usually towards a specific allergen.

"Respiratory viral infection" as used herein shall relate to an infection of the respiratory tract, particularly of the upper respiratory tract, caused by a virus, as defined by code group J00 of the International Classification of Diseases, version 10 (ICD-10).

The term "therapeutic treatment" as used herein shall mean any therapeutic intervention using a hyperosmolar preparation referred to herein that is applied to modify the clinical course of the stuffy nose and/or of the respiratory viral infection in such a way that either clinical symptoms such as runny nose, blocked nose, sore throat, sneezing, chilliness, headache, muscle ache, cough, etc., are less severe than without intervention; or in such a way that said clinical symptoms persist for shorter periods; or in such a way that the time period is shortened during which an infected individual having said symptoms remains capable of transmitting the infectious agents to another individual; or in such a way that relapses of the disease, i.e. periods without symptoms followed by periods with symptoms, occur less frequently; or in such a way that any combination of said effects may be obtained.

Likewise, in the context of the present invention, the term "prophylactic treatment" shall mean any intervention using a hyperosmolar preparation referred to herein that is applied to an individual in need thereof or having an increased risk of acquiring a respiratory tract infection, wherein said intervention is carried out prior to the onset of a viral infection and typically has in effect that either no viral infection occurs or no clinically relevant symptoms of a viral infection occur in a healthy individual upon subsequent exposure to an amount of infectious viral agent that would otherwise, i.e. in the absence of such a prophylactic treatment, be sufficient to cause a respiratory viral infection.

The term "prophylactic treatment" shall also encompass an intervention prior to the onset of a respiratory tract infection and using a hyperosmolar preparation referred to herein that delivers a partial effect only, i.e. wherein in spite of a prophylactic treatment of the nose a respiratory viral infection develops, however with symptoms that are less severe than without a prophylactic treatment, or with symptoms that show a delayed onset or resolve earlier.

Accordingly, the hyperosmolar nose-deblocking composition referred to herein comprising iota and/or kappa carrageenan is also active against a respiratory tract disease caused by an infection with a virus selected from the group consisting of human rhinovirus, human coronavirus, a member of the paramyxoviridae such as parainfluenza virus, metapneumovirus, or respiratory syncytial virus, a member of the orthomyxoviridae such as influenza virus, or an adenovirus subtype B (ICD-10 codes J09 and J10). The diseases caused are usually referred to as common cold, flu-like disease, or influenza.

In a preferred embodiment herein, the hyperosmolar pharmaceutical composition developed for deblocking a stuffy nose and for simultaneously treating respiratory viral infections is specifically adapted for topical administration to the nasal cavity.

The hyperosmolar pharmaceutical composition may be applied before or after the outbreak of a respiratory viral infection in a human individual. Even if applied after the outbreak of a viral infection it may still prevent or at least ameliorate late complications of respiratory viral infections. Such complications are known in the art and include—but are not limited to—complications in connection with secondary infections by bacteria, and deterioration of pre-existing diseases such as allergy or COPD.

The hyperosmolar composition referred to herein typically contains a carrageenan component, preferably iota-carrageenan or a combination of iota- and kappa-carrageenan, as an active antiviral ingredient or—as the case may be—as the sole active antiviral ingredient, at a concentration of from 0.05% to 1% weight by volume (g/L), preferably of from 0.1 to 0.5%, and most preferably of from 0.1 to 0.3% w/v of the ready-for-use preparation. Its osmolality is adjusted to a value of greater than 300 mOsm/kg, preferably to a value within a range of from 500 mOsm/kg to 1000 mOsm/kg, most preferably to a value of from 650 to 900 mOsm/kg. The composition does not contain more than 1.5% sodium chloride, preferably not more than 1.2% sodium chloride, most preferably not more than 0.9% and frequently less than 0.9% w/v of sodium chloride as a ionic osmolality giver.

Where the term "slightly hyperosmolar" is used herein in connection with an ionic osmolality giver it shall be understood as to refer to a sodium chloride concentration of between 0.9% to 1.5% w/v, or to an equivalent, i.e. equimolar, concentration of another ionic osmolality giver.

The adjustment of hyperosmolality is accomplished by adding at least one of a low molecular weight sugar and a low molecular weight polyvalent alcohol ("polyol") to a physiologically acceptable aqueous solution, typically comprising a carrageenan component as disclosed herein. Suitable sugars may be selected from the group of monosaccharides, disaccharides, and oligosaccharides, and typically from glucose, fructose, mannose, and sucrose. Suitable polyvalent alcohols, typically short-chain sugar alcohols having a backbone of 3 to 12 carbon atoms, may be selected from the group of glycerol, erythritol, sorbitol, mannitol, xylitol, threitol, inositol, and maltitol. The osmolality adjusting agents sorbitol, mannitol, or glucose are typically used at a concentration of from 0.5% to 20%, preferably of from 2% to 15%, most preferably of from 3% to 10% weight by volume, i.e grams per liter.

Topically administrable intranasal compositions referred to herein may have a pH value within a range of from 3.5 to 8.0, usually within a range of from about 4.0 to about 8.0. They may comprise one or more nasally compatible pH adjusting agents or buffer systems that prevent pH drift during storage. Such pH adjusting agents include, but are not limited to, boric acid, sodium borate, potassium citrate, citric acid, sodium bicarbonate, and various inorganic phosphate buffers such as $Na_2HPO_4$, $NaH_2PO_4$, $KH_2PO_4$, and mixtures thereof. The minimal ionic strengths introduced by any such pH-adjusting agents do not interfere with the essence of the invention. To prevent precipitation of calcium with phosphate ions from the buffer system, EDTA may be added up to a concentration of 2 mg/ml. In addition, flavors such as eucalyptus, campher, menthol, peppermint or similar, by way of oils or extracts, may be added to the product at concentrations known in the art.

Also, the topical intranasal formulations referred to herein may comprise one or more intranasally compatible surfactants. The surfactant facilitates the spread of the formulation across the surface of the nasal mucosa, and may be non-ionic or anionic. Exemplary non-ionic surfactants may be selected from the group comprising tyloxapol, polyoxyethylene sorbitan esters, polyethoxylated castor oils, poloxamers, polyoxyethylene/polyoxypropylene surfactants, polyoxyethylene stearate, polyoxyethylene propylene glycol stearate, hydroxyalkylphosphonate, lauric or palmitic acid esters and ethers, triethanol amine oleate, or from a combination of the foregoing agents. Still further suitable surfactants may be known to those skilled in the art. The surfactants may typically be present at concentrations of from 0.02% (w/v) to 0.1% (w/v) of the composition.

In various embodiments, the present topical intranasal preparation may contain one or more preservatives to inhibit microbial growth and to prolong shelf life. Exemplary preservatives include, but are not limited to, disodium edetate (EDTA) and potassium sorbate. The preservative amount is typically less than about 0.02% (w/v) of the total composition, EDTA may be added up to 2 mg/ml.

In addition to the ingredients mentioned above, it is contemplated that a variety of additional or alternative ingredients may be present in the pharmaceutical compositions of the present invention, which additional or alternative ingredients include anti-oxidants such as vitamin E or its commercially available derivatives such as tocopherol polyethylene glycol 1000 succinate (TPGS), ascorbic acid, or sodium metabisulfite.

The pharmaceutical compositions herein are typically provided in sterile form for topical administration to the nasal cavity, and are preferably adjusted for self-administration by the individual in need thereof. In one embodiment, the preparation is a particle-free nasal spray. Other suitable galenic formulations include intranasally acceptable swabs, as well as ointments and gels that can be applied to the nose, optionally as sprays or aerosols.

Example 1: Determination of $IC_{50}$ Values of Carrageenan for Human Rhinovirus 1a and 8

Hela cells were seeded into 96 well plates with a cell density of $5*10^3$ cells per well and cultivated for 24 hours in a standard DMEM tissue culture medium containing 4.5 g/l glucose. Virus suspensions containing carrageenan polymer at varying concentrations of between 0 and 150 µg/ml, in combination with NaCl and sorbitol (as indicated in the respective legends to each table) in a dilution series, were incubated for 30 minutes. Cells were infected with these virus suspensions containing the test substances and $7*10^3$ (HRV1a) or $5*10^4$ (HRV8) infectious units per well. 30 minutes after infection the virus inoculum was removed and substituted by virus-free infection medium containing carrageenan polymer, NaCl salt and sorbitol in the concentrations to be tested. The cells were incubated for 2 to 3 days at 33° C. The antiviral efficacy of the test samples was assessed by determining cell viability when more than 90% cells of a control infection in the absence of a carrageenan polymer had died. An incubation of cells with the same dilution series of test substances (i.e. carragenan component plus osmolalitiy adjusting agents) in the absence of viral infection was performed to monitor for a potential toxicity of the treatment. Calculation of $IC_{50}$ values was performed with standard fitting software ExcelFit. No significant negative effect of the polymer and of the different tested salt or sorbitol concentrations on the uninfected cells was detected.

TABLE 1

Increase of $IC_{50}$ values of iota carrageenan on two types of human rhinovirus dependent on the concentrationof NaCl compared to a hypoosmolar solution (0.5% NaCl; osmolality = 174 mOsm/kg); * = significant difference of $IC_{50}$ values compared to the 0.5% formulation; ns = non-significant difference compared to the 0.5% formulation.

|  | 0.9% NaCl | 2% NaCl | 2.3% NaCl | 2.6% NaCl |
| --- | --- | --- | --- | --- |
| osmolality | 295 mOsm/kg | 670 mOsm/kg | 776 mOsm/kg | 872 mOsm/kg |
| HRV1a inhibition | 3.1-fold* | 14.5-fold* | 22.3-fold* | 33.7-fold* |
| HRV8 inhibition | 1.8-fold (ns) | 3.6-fold* | 6.9-fold* | 7.5-fold* |

As shown in Table 1 the inhibition of human rhinovirus replication is strongly impaired by increasing NaCl concentrations in the iota-carrageenan preparations. By comparison of a hypoosmolar solution (0.5% NaCl) with isoosmolar (0.9%) and hyperosmolar solutions (2%, 2.3%, and 2.6% NaCl) a significant reduction in inhibitory efficacy of up to approximately 34-fold is observed.

As shown in Table 2 the antiviral efficacy is retained when 7% sorbitol is added to a 0.5% or 0.9% NaCl solution to achieve the desired increased osmolality of the solution.

TABLE 2

Increase of $IC_{50}$ values of a carrageenan blend (iota-carrageenan/kappa carrageenan 3:1 w/w) in hyperosmolar solutions on human rhinovirus 1a and 8 compared to a hypoosmolar solution (0.5%; osmolality = 174 mOsm/kg); * = significant difference of $IC_{50}$ values compared to the 0.5% formulation; ns = non-significant difference compared to the 0.5% formulation.

|  | 0.5% NaCl + 7% sorbitol | 0.9% NaCl + 7% sorbitol | 2.3% NaCl |
|---|---|---|---|
| osmolality | 597 mOsm/kg | 733 mOsm/kg | 748 mOsm/kg |
| HRV1a inhibition | 1.2-fold (ns) | 1.8-fold (ns) | 33-fold* |
| HRV8 inhibition | 1.3-fold (ns) | 1.6-fold (ns) | 3.8-fold* |

In order to achieve a formulation with a stable pH, 0.5-fold Mc-Ilvaine buffer (phosphate/citrate buffer) with 1 mg/ml EDTA was added to the carrageenan solutions containing 0.5% or 0.9% NaCl plus 7% or 10% sorbitol. The pH, osmolality and viscosity of these solutions were determined.

Table 3 below represents the decrease in $IC_{50}$ of carrageenan preparations (blend iota-carrageenan/kappa carrageenan in a ratio of 3:1 w/w) prepared according to the invention as compared to a carrageenan preparation containing 2.3% NaCl as the sole osmolality adjusting agent. As shown in Table 3, the hyperosmolar formulation of carrageenan comprising 0.5% or 0.9% NaCl, 7% sorbitol with 0.5-fold Mc-Ilvaine buffer and 1 mg/ml EDTA is far superior to the formulation of carrageenan with 2.3% NaCl only. The osmolality values of the solutions comprising sorbitol are close to the value obtained with 2.3% saline that is commonly applied with hyperosmolar nasal sprays to obtain a decongestant activity.

TABLE 3

Dramatic decrease of $IC_{50}$ values of carrageenan blend (iota-carrageenan/kappa carrageenan 3:1) in a buffered hyperosmolar solution on human rhinovirus 8 as compared to the virus inhibitory efficacy of a 2.3% NaCl hyperosmolar carrageenan solution (osmolality = 904 mOsm/kg); * = significant reduction of $IC_{50}$ values compared to the 2.3% saline formulation.

|  | 0.5% NaCl + 7% sorbitol | 0.9% NaCl + 7% sorbitol |
|---|---|---|
| osmolality | 787 mOsm/kg | 904 mOsm/kg |
| HRV1a inhibition | 153-fold* | 84.9-fold* |
| HRV8 inhibition | 6.7-fold* | 5.4-fold* |

Example 2: Procedure for Determining the Minimal Inhibitory Concentration of Iota-Carrageenan for the Prevention of Human Coronavirus OC43 Attachment (Hemagglutination Inhibition Assay)

On a 96-well plate, two hemagglutination units of hCoV OC43/well were incubated with a ½-log dilution series of test or control samples for 10 min at room temperature. Final assay concentrations were 0.002 to 3 µg/ml iota-carrageenan in aqueous 0.5, 0.9, 2.0, 2.3 or 2.6% NaCl solution in the presence or absence of 7% sorbitol. Then, a suspension of chicken RBCs (1% v/v in PBS) was added to each well to allow hemagglutination of red blood cells (RBCs) by the virus for 1.5 hrs at 4° C. At the time point of assay evaluation, control RBCs in the absence of carrageenan were fully agglutinated, whereas hemagglutination was inhibited in the presence of carrageenan up to a sample-specific concentration, the minimal inhibitory concentration.

As shown in Tables 4 and 5, carrageenan formulations containing increased concentrations of sodium chloride (2%, 2.3%, and 2.6%) are far less effective in preventing the attachment of human coronavirus OC43 to erythrocytes. The replacement of sodium chloride with sorbitol reverts this effect and no significant difference to a hypoosmolar carrageenan solution containing 0.5% sodium chloride is detected.

TABLE 4

Increase of the minimal inhibitory concentration of iota-carrageenan on human coronavirus OC43 dependent on the concentration of NaCl compared to hypoosmolar solution (0.5%; osmolality = 174 mOsm/kg); * = significant difference of the minimal inhibitory concentration compared to the 0.5% formulation; ns = non-significant difference compared to the 0.5% formulation

|  | 0.9% NaCl | 2% NaCl | 2.3 NaCl | 2.6% NaCl |
|---|---|---|---|---|
| osmolality | 295 mOsm/kg | 670 mOsm/kg | 776 mOsm/kg | 872 mOsm/kg |
| hCV OC43 | 1-fold (ns) | 10-fold* | 10-fold* | 10-fold* |

TABLE 5

Increase of the minimal inhibitory concentration of iota-carrageenan in hyperosmolar solutions on human coronavirus OC43 compared to a hypoosmolar solution (0.5%; osmolality = 174 mOsm/kg); * = significant difference of the minimal inhibitory concentration compared to the 0.5% formulation; ns = non-significant difference compared to the 0.5% formulation.

|  | 0.5% NaCl + 7% sorbitol | 0.9% NaCl + 7% sorbitol | 2.3% NaCl |
|---|---|---|---|
| osmolality hCV OC43 | 597 mOsm/kg 1-fold (ns) | 733 mOsm/kg 1-fold (ns) | 748 mOsm/kg 10-fold* |

Example 3: Sterile Filtration of Hyperosmolar Solutions Containing Carrageenan

As summarized in Table 6, sterile filtration of hyperosmolar solutions containing carrageenan is impaired in case of high concentrations of sodium chloride. The addition of 7% or 10% sorbitol as an alternative osmolality giver has a similar effect in some preparations, i.e. these solutions cannot be sterile filtered through a 0.22 µm filter system either. In contrast, all hyperosmolar carrageenan formulations that contain additional buffer and EDTA can be sterile filtered through a 0.22 µm filter. Therefore, a carrageenan formulation containing a non-ionic osmolality adjusting agent, such as sorbitol, in partial or full replacement of an ionic osmolality adjusting agent, such as sodium chloride, together with a suitable buffer plus EDTA, can be produced as a sterile solution that is effective in deblocking a stuffy nose and remains antivirally active against at least human rhinoviruses.

TABLE 6

Summary of hyperosmolar carrageenan preparations containing different amounts of sodium chloride, sorbitol and different amounts of buffer plus EDTA. The osmolality and the pH of the preparations was determined. The possibility for sterile filtration through a 0.22 μm filter was tested. Xylitol and mannitol may be substituted for sorbitol to yield comparable results with regard to sterile filtration and therapeutic efficacy (data not shown).

| Preparation No. | iota carr. [%] | kappa carr. [%] | Sorbitol [%] | NaCl [%] | McIlvaine + 1 mg/ml EDTA pH 6.0 [x-fold] | Osmolality [mOsm/kg] | pH (RT) | sterile filtration possible |
|---|---|---|---|---|---|---|---|---|
| 1 | 0.12 | 0.04 | 0 | 2.0 | 0 | 670 | 6.97 | yes |
| 2 | 0.12 | 0.04 | 0 | 2.3 | 0 | 776 | 7.33 | no |
| 3 | 0.12 | 0.04 | 0 | 2.6 | 0 | 872 | 7.18 | no |
| 4 | 0.12 | 0.04 | 7 | 0.5 | 0.25 | 719 | 5.93 | yes |
| 5 | 0.12 | 0.04 | 10 | 0.5 | 0.25 | 954 | 5.91 | yes |
| 6 | 0.12 | 0.04 | 7 | 0.9 | 0.25 | 829 | 5.85 | yes |
| 7 | 0.12 | 0.04 | 10 | 0.9 | 0.25 | 1090 | 5.83 | yes |
| 8 | 0.12 | 0.04 | 7 | 0.5 | 0.5 | 787 | 5.98 | yes |
| 9 | 0.12 | 0.04 | 7 | 0.9 | 0.5 | 904 | 5.91 | yes |
| 10 | 0.12 | 0.04 | 0 | 2.3 | 0.25 | 829 | 5.70 | yes |
| 11 | 0.12 | 0.04 | 0 | 2.3 | 0.5 | 904 | 5.80 | yes |
| 12 | 0.12 | 0.04 | 7 | 0.5 | 0 | 597 | 6.64 | no |
| 13 | 0.12 | 0.04 | 7 | 0.9 | 0 | 733 | 6.61 | no |
| 14 | 0.12 | 0 | 7 | 0.5 | 0 | 595 | 6.46 | yes |
| 15 | 0.12 | 0 | 7 | 0.9 | 0 | 706 | 6.76 | yes |
| 16 | 0.12 | 0 | 7 | 0.5 | 0.25 | 670 | 5.94 | yes |
| 17 | 0.12 | 0 | 10 | 0.5 | 0.25 | 877 | 5.93 | yes |
| 18 | 0.12 | 0 | 7 | 0.9 | 0.25 | 801 | 5.86 | yes |
| 19 | 0.12 | 0 | 10 | 0.9 | 0.25 | 1021 | 5.84 | yes |
| 20 | 0.12 | 0 | 7 | 0.5 | 0.5 | 755 | 5.99 | yes |
| 21 | 0.12 | 0 | 7 | 0.9 | 0.5 | 889 | 5.92 | yes |

In addition, eucalyptus aroma may be added to the composition as a flavoring agent, typically at usual concentrations in a range of from 0.01-0.05 ml/L, for example of from 0.02-0.03 ml/L (0.002-0.003% v/v) of the final composition.

Also, dexpanthenol may be added as a humectant, emollient, and/or moisturizer at concentrations typically ranging from 1-5% v/v of the final composition. Dexpanthenol is also known to improve hydration, to reduce itching and inflammation of the skin, and to accelerate the rate of healing of epidermal wounds.

Example 4: Antiviral Active and Decongestant Nasal Spray Preparation

Iota-carrageenan: 1.2 mg/ml
Kappa-carrageenan: 0.4 mg/ml
Sorbitol: 70 mg/ml
NaCl: 5 mg/ml
0.5-fold Mc-Ilvaine buffer
1 mg/ml EDTA
Osmolality: 787 mOsm/kg
Water ad 100%

Example 5: Antiviral Active and Decongestant Nasal Spray Preparation

Iota-carrageenan: 1.2 mg/ml
Kappa-carrageenan 0.4 mg/ml
Sorbitol: 70 mg/ml
NaCl: 9 mg/ml
0.5-fold Mc-Ilvaine buffer
1 mg/ml EDTA
Osmolality: 904 mOsm/kg
Water ad 100%

Example 6: Antiviral Active and Decongestant Nasal Spray Preparation

Iota-carrageenan: 1.2 mg/ml
Kappa-carrageenan: 0.4 mg/ml
Sorbitol: 100 mg/ml
NaCl: 5 mg/ml
0.25-fold Mc-Ilvaine buffer
1 mg/ml EDTA
Osmolality: 954 mOsm/kg
Water ad 100%

Example 7: Antiviral Active and Decongestant Nasal Spray Preparation

Iota-carrageenan: 1.2 mg/ml
Kappa-carrageenan: 0.4 mg/ml
Sorbitol: 100 mg/ml
NaCl: 9 mg/ml
0.5-fold Mc-Ilvaine buffer
1 mg/ml EDTA
Osmolality: 1090 mOsm/kg
Water ad 100%

In Examples 4-7 sorbitol may be partially or fully replaced with equimolar concentrations of xylitol and/or mannitol without resulting in a significant difference in nose deblocking and/or antiviral efficacy of the respective preparations (data not shown).

Example 8: Nose Deblocking Effect

Ten patients reporting a blocked nose for more than 12 hours due to a flu-like infection of the upper respiratory tract were treated with a preparation manufactured according to Example 4 (preparation no. 8 in Table 6). 140 µl of the preparation were applied to each nostril with a standard nasal spray pumping device. Within 2 minutes after the application the volunteers reported an improvement of the stuffy nose symptom and after 5 minutes all volunteers were able to breath freely through the nose. The decongestant effect was sustainably felt by the volunteers for more than 1 hour. Half of the volunteers even reported a sustained relief of symptoms until 4 hours post administration.

What is claimed is:

1. A hyperosmolar aqueous solution which has an immediate stuffy nose deblocking activity and which is active against viral infections of the respiratory tract, wherein:
   the hyperosmolar aqueous solution comprises a non-ionic osmolality adjusting agent in combination with an ionic osmolality adjusting agent, and a carrageenan component as an active antiviral ingredient in an antivirally effective amount;
   the hyperosmolar aqueous solution includes a nasally compatible buffer and has a pH value of from 4.0 to 8.0;
   the hyperosmolar aqueous solution includes EDTA at a concentration of up to 2 mg/ml;
   the ionic osmolality adjusting agent is selected from the group consisting of sodium chloride, potassium chloride, and a mixture of sodium and potassium chloride;
   a total concentration of the non-ionic and ionic osmolality adjusting agents is such that the hyperosmolar aqueous solution has a hyperosmolar osmolality value of from 500 mOsm/kg to 1000 mOsm/kg;
   the carrageenan component is the sole antiviral active ingredient in the hyperosmolar aqueous solution and is selected from the group consisting of iota-carrageenan, kappa-carrageenan, and a mixture of iota- and kappa carrageenan; and
   a concentration of the carrageenan component is from 0.05% to 1% weight by volume (g/L) of a formulation of the hyperosmolar aqueous solution that is to be administered;
   with the proviso that the hyperosmolar aqueous solution in the formulation that is to be administered contains no more than 1.5% w/v of a said ionic osmolality adjusting agent.

2. The hyperosmolar aqueous solution of claim 1, wherein the non-ionic osmolality adjusting agent is selected from the group consisting of monosaccharides, disaccharides, oligosaccharides, and low molecular weight polyols, and wherein the low molecular weight polyols are selected from the group consisting of glycerol, erythritol, mannitol, sorbitol, inositol, xylitol, threitol, and maltitol.

3. The hyperosmolar aqueous solution of claim 2, wherein the mono- and disaccharides are selected from the group consisting of glucose, fructose, sucrose, and mannose.

4. The hyperosmolar aqueous solution of claim 1, wherein the hyperosmolar aqueous solution further comprises at least one physiologically acceptable additive selected from the group consisting of a preservative, an anti-oxidant, a humectant, an emollient, a moisturizer, and a flavoring agent.

5. The hyperosmolar aqueous solution of claim 1, wherein the hyperosmolar aqueous solution comprises the non-ionic osmolality adjusting agent in a concentration of from 1 to 15% w/v of the hyperosmolar aqueous solution.

6. The hyperosmolar aqueous solution of claim 1, wherein the hyperosmolar aqueous solution comprises the ionic osmolality adjusting agent at a concentration of from 0.1 to 1.3% w/v of the hyperosmolar aqueous solution.

7. The hyperosmolar aqueous solution of claim 1, for use as a medicament.

8. The hyperosmolar aqueous solution of claim 1, for use as a stuffy nose deblocking agent.

9. The hyperosmolar aqueous solution of claim 7, for use as an antiviral agent in the prophylactic or therapeutic treatment of viral infections of the upper respiratory tract.

10. The hyperosmolar aqueous solution of claim 9, wherein the viral infections are selected from the group consisting of infections caused by human rhinovirus, human coronavirus, members of the paramyxoviridae, members of the orthomyxoviridae and adenovirus subtype B.

11. The hyperosmolar aqueous solution of claim 1, in a form for topical administration.

12. The hyperosmolar aqueous solution of claim 1, wherein the hyperosmolar aqueous solution comprises the non-ionic osmolality adjusting agent in a concentration of from 5 to 10% w/v of the hyperosmolar aqueous solution.

13. The hyperosmolar aqueous solution of claim 1, wherein the hyperosmolar aqueous solution comprises the ionic osmolality adjusting agent at a concentration of from 0.5 to 1.2% w/v of the hyperosmolar aqueous solution.

14. The hyperosmolar aqueous solution of claim 9, wherein the viral infections are selected from the group consisting of infections caused by parainfluenza virus, metapneumovirus, and respiratory syncytial virus.

15. The hyperosmolar aqueous solution of claim 9, wherein the viral infections are selected from the group consisting of infections caused by influenza A and B virus.

16. The hyperosmolar aqueous solution of claim 1, in a form of a nasal spray.

17. The hyperosmolar aqueous solution of claim 1, in a form of a medicament for immediate unblocking of a congested nose and simultaneous treatment of a viral infection of the upper respiratory tract.

18. The hyperosmolar aqueous solution of claim 1, wherein the hyperosmolar aqueous solution includes the EDTA at a concentration of from 1 to 2 mg/ml.

19. The hyperosmolar aqueous solution of claim 1, wherein the total concentration of the non-ionic and ionic osmolality adjusting agents is such that the hyperosmolar aqueous solution has a hyperosmolar osmolality value of from 650 to 900 mOsm/kg.

20. The hyperosmolar aqueous solution of claim 1, wherein the concentration of the carrageenan component is from 0.1% to 0.3% weight by volume (g/L) of the formulation that is to be administered.

* * * * *